US011707638B2

(12) United States Patent
Zwolinsky et al.

(10) Patent No.: US 11,707,638 B2
(45) Date of Patent: *Jul. 25, 2023

(54) POWERED AIR BREATHING APPARATUS

(71) Applicant: 3M INNOVATIVE PROPERTIES COMPANY, St. Paul, MN (US)

(72) Inventors: Albert F. Zwolinsky, Skelmersdale (GB); Richard D. Marshall, Skelmersdale (GB); Christopher G. Hall, Skelmersdale (GB)

(73) Assignee: 3M Innovative Properties Company, St. Paul, MN (US)

( * ) Notice: Subject to any disclaimer, the term of this patent is extended or adjusted under 35 U.S.C. 154(b) by 420 days.

This patent is subject to a terminal disclaimer.

(21) Appl. No.: 16/878,686

(22) Filed: May 20, 2020

(65) Prior Publication Data
US 2020/0276461 A1 Sep. 3, 2020

Related U.S. Application Data

(63) Continuation of application No. 15/893,981, filed on Feb. 12, 2018, now Pat. No. 10,695,592, which is a (Continued)

(30) Foreign Application Priority Data

| Nov. 2, 2009 | (GB) | 0919211 |
| Nov. 3, 2009 | (GB) | 0919277 |
| Mar. 29, 2010 | (GB) | 1005293 |

(51) Int. Cl.
*A62B 9/00* (2006.01)
*A62B 18/00* (2006.01)
(Continued)

(52) U.S. Cl.
CPC ......... *A62B 9/006* (2013.01); *A61M 16/0051* (2013.01); *A61M 16/0066* (2013.01);
(Continued)

(58) Field of Classification Search
CPC .... A61M 16/00–0003; A61M 16/0051; A61M 16/0057–0081
See application file for complete search history.

(56) References Cited

U.S. PATENT DOCUMENTS

| 5,950,621 A | 9/1999 | Klockseth |
| 6,186,140 B1 | 2/2001 | Hoague |

(Continued)

FOREIGN PATENT DOCUMENTS

| EP | 0916369 | 5/1999 |
| EP | 2070563 | 6/2009 |

(Continued)

OTHER PUBLICATIONS

Extended European Search Report for corresponding European Application No. 16183883.4 dated Nov. 3, 2016, 5 pages.

*Primary Examiner* — Rachel T Sippel
(74) *Attorney, Agent, or Firm* — Steven A. Bern; Dena M. Ehrich

(57) ABSTRACT

A safety breathing apparatus has a sensor for measuring the difference in pressure between two point 1a, 1b in the gas delivered to a head unit 9. The sensor is used to measure the difference in the pressure of the gas supplied through the apparatus between the two points in the gas flow, and the pressure difference is then used to calculate the gas flow rate.

8 Claims, 5 Drawing Sheets

Related U.S. Application Data continuation of application No. 15/178,717, filed on Jun. 10, 2016, now Pat. No. 10,668,307, which is a continuation of application No. 13/521,024, filed as application No. PCT/GB2010/051803 on Oct. 27, 2010, now Pat. No. 9,387,299.

(51) Int. Cl.

| | |
|---|---|
| *A61M 16/00* | (2006.01) |
| *A61M 16/06* | (2006.01) |
| *A61M 16/10* | (2006.01) |
| *A62B 18/02* | (2006.01) |
| *A62B 9/04* | (2006.01) |
| *A61M 16/08* | (2006.01) |
| *A62B 7/02* | (2006.01) |
| *A62B 7/10* | (2006.01) |
| *A62B 18/08* | (2006.01) |

(52) U.S. Cl.
CPC .......... *A61M 16/024* (2017.08); *A61M 16/06* (2013.01); *A61M 16/0875* (2013.01); *A61M 16/105* (2013.01); *A62B 7/02* (2013.01); *A62B 7/10* (2013.01); *A62B 9/04* (2013.01); *A62B 18/006* (2013.01); *A62B 18/02* (2013.01); *A62B 18/088* (2013.01)

(56) References Cited

U.S. PATENT DOCUMENTS

| | | |
|---|---|---|
| 6,997,206 B1 | 2/2006 | Klockseth |
| 2003/0180149 A1 | 9/2003 | Krugerke |
| 2005/0108057 A1 | 5/2005 | Cohen |
| 2005/0183721 A1 | 8/2005 | Juergensen |
| 2005/0234310 A1 | 10/2005 | Alwan |
| 2005/0263155 A1 | 12/2005 | Goddweiler |
| 2006/0090754 A1 | 5/2006 | Mittelstadt |
| 2007/0144519 A1 | 6/2007 | Henry |
| 2007/0265877 A1 | 11/2007 | Rice |
| 2008/0066754 A1* | 3/2008 | Faram ............... A61M 16/0063 128/204.25 |
| 2010/0147301 A1 | 6/2010 | Kwok |

FOREIGN PATENT DOCUMENTS

| | | |
|---|---|---|
| GB | 2336319 | 10/1999 |
| WO | WO 1996-026116 | 8/1996 |
| WO | WO 2001-080952 | 2/2001 |
| WO | WO 2002-011815 | 2/2002 |
| WO | WO 2009-020765 | 2/2009 |
| WO | WO 2009-029326 | 3/2009 |

* cited by examiner

POWERED AIR BREATHING APPARATUS

CROSS REFERENCE TO RELATED APPLICATIONS

This application is a continuation of U.S. application Ser. No. 15/893,981 filed Feb. 12, 2018, allowed, which is a continuation of U.S. application Ser. No. 15/178,717, filed Jun. 10, 2016, which is a continuation of U.S. application Ser. No. 13/521,024, filed Jun. 17, 2013, now U.S. Pat. No. 9,387,299, which is a 371 of PCT/GB2010/051803, filed Oct. 27, 2010, which claims the benefit of GB applications 0919211.3, filed Nov. 2, 2009, 0919277.4, filed Nov. 3, 2009 and 1005293.4, filed Mar. 29, 2010, the disclosure of each of which is incorporated by reference in their entirety herein.

The present invention relates to improvement to powered air filtering devices incorporating a helmet, mask or hood with particulate, gas or combination filters for respiratory protection.

It has been recognized that it is advantageous to monitor and measure the flow rate of air into a powered air respirator. This is because monitoring of the flow rate enables checks to be made to ensure that the filter flow rate capability is not exceeded, thus ensuring that the filter effectively filters all contaminants from the breathable air delivered to the wearer. Furthermore, the air delivery control system can use a closed loop flow measurement system maintain a given flow rate to the user irrespective of changes in conditions such as changes in the filter resistance or resistance of different headtop's or mask's worn by the user; changes in ambient air pressure resulting from, for example, variations in altitude and the like. Similarly, an active system can use the closed loop flow rate control to automatically compensate for the effects of breathing that constantly vary the load on the breathing air delivery fan assembly.

Modern respirators typically have a wide selection of accessories in the form of filter types, varying design of headtop or mask for different applications etc., and this gives rise to issues with maintaining a given flow rate across any combination of accessories. The atmosphere is, by its very nature, compressible, and thus as flow rates increase in a powered air respirator, the air compresses and a nonlinear relationship exists for flow rate and impeller speed. The flow resistance of a particular filter can also vary through its life as airborne particles are drawn into and retained on the filter medium, interfering with the movement of air therethrough and thus constantly increasing resistance through the filter life. Furthermore, the mere act of the user breathing causes variations in the load on the motor causing fluctuations in the flow rate. As the user breathes in, air is drawn through the filter, assisting the motor in supplying air and therefore effectively reducing the load. On the other hand, as the user breathes out, air flow is inhibited, even when a non-return valve is used, thereby increasing the load on the motor.

It is relatively easy to monitor the speed of the impeller during operation of the apparatus, and it has been suggested to use this to calculate the flow rate. However, the natural efficiency of a fan design varies with different loads placed on it by varying resistances on the air inlet side and on the loads on the air outlet side. As a result, the impellor speed has no direct correlation to the flow rate.

Despite this issue with correlation between impellor speed and flow rate, for simple devices, such as a face mask with a built-in fan and a limited choice of filter/s, it has been found that a very good approximation of flow rate can be made by comparing motor speed and motor load to create an algorithm of motor speed and load to estimate flow rate. It has also been known in the art to extend this approach to more complicated systems, but has meant that for a given filter or head top, the flow rate supplied by the respirator would be nearly constant but different for each combination. This approach also suffers from the drawback that it does not cater for changes resulting from variations in altitude (motor speed will increase as the density of the atmosphere decreases). In some models, these drawbacks can be alleviated by varying the number of filters that can be fitted in an attempt to reduce some of the filter resistance loading—as more filters are fitted, the filter resistance becomes lower and a balancing act commences on the number of filters to level out the inlet load on the respirator.

Another known approach is to increase all the lower load filters to the equivalent highest load filters thereby equalizing the input load. The added complication to all this is that as the resistance changes over the life of the filter, the load increases complicating the load and speed algorithm. Another approach which has been proposed is to calibrate the device using a rotameter, which is primarily a mass flow meter and thus varies with humidity and altitude effects on density.

Thus, it can be seen that prior art approaches have generally concentrated on approximation methods for flow rate and these have generally been found to be acceptable. However, as a result of filters getting more technical for different contamination challenges, a desire to maintain a flow rate regardless of the initial filter resistance and variations in filter resistance through its operating life, and a desire for different headtops to suit different applications, these approximation methods are now becoming insufficient.

Furthermore, analysis of the air within a typical powered air breathing apparatus assembly has shown that turbulence exists in the respirator assembly at flow rates that are required for breathing. This complicates any generally acceptable way of measuring airflow without the use of laminar air control system in place that causes a heavy load on the system either causing flow rates to be decreased and/or battery life of battery powered respirators to be reduced significantly.

According to the present invention there is provided a method of measuring the flow rate of gas supply in safety breathing apparatus comprising the steps of measuring the difference in the pressure of the gas supplied through the apparatus between at least two different points in the gas flow, and using said pressure difference to calculate the gas flow rate.

The present invention further provides a safety breathing apparatus having means for measuring the difference in pressure of gas being delivered by the apparatus between at least two different points in the gas flow, whereby the gas flow rate can be calculated from said pressure differential.

The apparatus and method in accordance with the invention has the advantage that by measuring pressure and using the differential to calculate the flow rate of gas through the apparatus, a much more accurate figure for the flow rate is obtained as compared with prior art systems without imposing a significant load on the air supply unit which would result in an increase in power requirements.

The pressure difference between the at least two points may be measured directly using a pressure differential gauge, such as by means of a diaphragm to opposing sides of which the pressure at each of the two points is supplied, deflection of the diaphragm measuring the pressure differential. Alternatively, the pressure may be directly measured at each point and the pressure differential between the points may then be calculated Preferably, a constriction is provided in the gas flow path, the pressure measurements being taken at the entry to and near the tightest part of the constriction. This has the advantage that the pressure differential between the two measurement points is increased, thereby reducing the pressure sensor sensitivity necessary to achieve accurate measurement of the flow rate. In particular, the constriction is formed by a plate orifice, a shaped nozzle and a venturi tube.

In a particularly preferred embodiment of the invention, a DALL tube is used to create the orifice. This has the advantage that it reduces the energy losses through the constriction considerably, which is important on a battery powered device where the operating life could be seriously impaired. In a further development of the present invention, pressure fluctuations caused by turbulent flow in the system are minimized by introducing dampening/filtering in the form of a mechanical filter to dampen the fluctuations although electrical filtering could also be used to average out spikes in the pressure differential measurement system.

Advantageously, a closed loop system is used to alter the motor speed based on the flow rate measurement to adjust the flow rate to reach or maintain the target value.

Modem safety legislation sets various stringent servicing, testing and use requirements for breathing apparatus in view of the potentially life-threatening implications of the failure of such equipment. It is important, for example, that a user only use equipment that he is trained to operate and that the correct equipment is used for the correct environment (use of a wrong filter, for example, can result in the wearer being exposed to harmful contaminants even though he is wearing the equipment correctly). Similarly, all equipment must be regularly serviced and tested to ensure it is operating properly.

Conventionally, monitoring of such requirements has been carried out manually—manual records being kept of the use time of equipment so as to enable service timetables to be calculated, and individual user checks being made m relation to equipment qualification/currency and correct application. Initiation Warranty, for example, is generally based on manufacturing date or by the user logging the purchase with the manufacturing company. Such manual systems are, however, subject to inaccuracies, etc. which can lead to servicing being carried out un-necessarily early or delayed causing possible health risk to users.

There is accordingly a need for an improved system which prevents operators using equipment they have not be trained to use or using incorrect equipment for the hazardous area they are in, and to provide accountability logging to ensure the product has been used appropriately in a hazardous environment. It is also an aim to provide a system which ensures that safety critical visual inspections and services are carried out at due times, and that data logs prove the operator has carried out those tasks. There is also a need to overcome Warranty Initiation delays inherent from manufacturing date to the user receiving the equipment, by providing an accurate record of when product was first used. By providing a very short delay time of say one hour to allow for demonstration of the product, the warranty can start after the defined run time delay.

Accordingly, the present invention further provides breathing apparatus having interchangeable components, each component having an identification means associated with it on which provides information unique to said component, the apparatus comprising a controller having a reader for reading the identification means of the or each component attached to the apparatus so as to identify said components.

Breathing apparatus in accordance with the invention has the advantage that, by reading information relating to each component removably attached to the apparatus, the controller is able to carry out checks such as compatibility of different components, service history or the like, and alert the use in the case that a problem is identified.

Preferably, the controller further includes a reader for reading a second identification means which provides information associated with the equipment user, the controller reading information from the or each first identification means and the second identification means, and checking for validity of the user to operate the equipment.

The identification means may carry a simple identification code unique to each device and or user, the controller being connected to a database which stores data related to users and devices and using the identification codes to look up the required data from the database. Each identification means may then be a barcode or the like, or may be an electronic storage means such as an RFID tag.

Each electronic storage means may be a wired storage medium which requires a direct connection with the reader for the reader to read data therefrom or may be a wireless medium such as an RFID chip. Each electronic storage means may store a simple ID tag which links to data stored in a central database or may store the full set of data relative to the component or user with which it is associated. In that case, the electronic storage means preferably has a write capability by means of which the controller is able to write information back to the storage means to enable an update of the data relating to the device with which it is associated. For example, the storage means may take the form of or at least include a flash memory device.

The second identification means is preferably a Tally Key/RFID chip which stores all information relating to the user with which it is associated. In one embodiment, the chip is mounted a coin type disk (in this application, but could also be a card or similar). The breathing apparatus then includes a mount for receiving the chip and securing mounting it on the apparatus. In particular, the mount is advantageously provided on a blower unit, the blower unit being inoperable until a chip has been mounted in place. The tally key is advantageously programmed with the information relating to permitted equipment types for the user, filter types allowed to be used, flow rate adjustment capability, pre-warning times and other suitable parameters. This tally key then becomes "persona}' and can be moved from one product to another to ensure operating parameters remain constant for the user.

Each first identification means advantageously stores operation information for the device with which it is associated, such as Service/Inspection Status using a real-time clock inside the controller or accessing real time clock from an external source. In this way, actual usage time can be used to identify when service and inspection is required. Each unit can be programmed to have visual safety inspections and services as required by the end user and or the manufacturer, at these preset periods, a warning will warn the user or prevent the user from further use of the product until the inspection or service has been carried out. Some allowances are built in to ensure that the product does not stop during use. For visual inspections by the user, the user will need to confirm the visual inspection has been carried out and the system will log the user from the tally key and record the date, time and user who carried out the visual inspection.

Services will be done by an approved service department who will log into the blower relevant information and clear the warning flag. Warranty Initiation Using the real-time clock, when the product is run for longer than the preset time, the warranty will be initiated in the blower and logged providing an absolute time/date of first use to prevent arguments over warranty start.

It has not hitherto been known to provide a Tally Key (RFID) system as taught in the invention. Service/Inspection Status This is generally carried out by manual documentation Warranty Initiation Warranty is generally based on manufacturing date or by the user logging the purchase with the manufacturing company.

Alarms are used to in breathing apparatus to bring to the attention of a user potentially life-threatening issues such as low battery life and the like. The use of audible alarms is conventional in the art, but in a work environment with many users, it is often difficult to identify the source of audible alarms and this can result in each user ignoring the alarm on the assumption that it actually relates to another user. Visual alarms have also been tried and can work, but part of the equipment can often be located out of the line of sight of the user (the field of view generally being reduced by the breathing mask itself). For example, a PAPR unit is generally carried on an operator's back and cannot be easily seen, so that a visual alarm provided on such a unit would be unlikely to be noticed by the user and it would, instead, be necessary to rely on surrounding user to inform the wearer of the alarm.

The present invention therefore further provides breathing equipment having a control unit and an alarm operable by the control unit to attract the attention of a user, wherein the alarm is a vibration alarm which communicates with the user through touch.

Breathing equipment incorporating a vibration alarm in accordance with the invention has the advantage that it came reliably gain the attention of the user to a possible risk situation in a manner which avoids the possibility of the alarm being overlooked, for example in noisy environments, or ignored because the user thinks it has originated from equipment other than his own.

Various forms of vibration alarm suitable for application to the invention are known in the art-for example a weight eccentrically mounted on a motor shaft which is rotated to activate the alarm. However, the exact form of the vibration alarm is not important to the invention.

The wide range of different applications and environments in which modern safety breathing apparatus is used necessitates modular type systems in which different components can be connected to meet the use requirements of an environment. Most commonly, a range of different filters will be available for each mask to enable a generic mask to be used in different environments having different filter requirements and also to enable a worn-out filter to be replaced. Prior art system typically uses a thread based or bayonet type system for attaching a filter and rely on frictional engagement when the thread or bayonet is fully engaged to retain the filter and prevent it being accidentally removed or loosened to an extent which could result in contaminated air making its way to the user. It has been known to use a compliant latch based locking system, which latch is urged out of the way as the filter is screwed into place and then latches back in when the filter is fully inserted. However, this system is still a fully rotation based system—removal of the filter still only requires counter rotational movement of the filter, albeit with an increased initial force sufficient to move the latch outwards to release the filter to unscrew.

According to the present invention there is provided a system for releasably attaching a filter to breathing apparatus comprising complementary male and female rotatably connecting coupling parts provided on the filter and breathing apparatus, and an interlock provided on at least one of the filter and the breathing apparatus, the interlock being moveable between a retracted position in which it is withdrawn from the coupling parts so as to allow rotation therebetween, and an engaged position in which it extends between the coupling parts so as to prevent relative rotation therebetween.

According to a further aspect of this part of the invention there is provided a filter having one part of a male and female rotational coupling formed thereon, and further having one part of an interlock system, which, in use, cooperates with a complementary part of an interlock system provided on a piece of breathing apparatus to prevent relative rotation between the filter and the breathing apparatus.

A still further aspect of this part of the invention provides a piece of breathing apparatus having one part of a male and female rotational coupling formed thereon, and further having one part of an interlock system, which, in use, cooperates with a complementary part of an interlock system provided on a filter to prevent relative rotation between the filter and the breathing apparatus.

The system of this part of the invention has the advantage that the interlock provides a positive and active lock between the filter and the breathing apparatus which requires additional manual actuation by a user before the filter can be rotated for removal from the breathing apparatus, thereby preventing accidental loosening or removal of the filter. The user has a definite indication that the filter is locked in place.

The rotational coupling may be a thread coupling or a bayonet type coupling, and is preferably configured with the female part of the coupling being provided in the breathing apparatus and the male part on the filter. It will, however, be understood that the reverse configuration is also possible, i.e. with the male part being provided on the breathing apparatus.

The interlock system preferably includes biasing means which biases one of the parts of the interlock system into the engaged position, said one part being moveable against the load of the biasing means into the retracted position in order to allow rotation between the filter and the breathing apparatus. In a particularly preferred embodiment, the interlock system comprises a peg mounted in one of the filter and the breathing apparatus (preferably in the breathing apparatus) so as to be radially movable between the retracted and extended positions, and an opening in the other of the other of the filter and the breathing apparatus size to receive the peg, opening aligning with the pin when the filter is fully engaged with the breathing apparatus so as to allow the pin to extend into the opening and thereby prevent further rotation of the filter relative to the breathing apparatus in either direction. Alternatively, the interlock could take the form of an axially moveable pin which is engageable between a pair of keyways provided in the coupling parts so as to prevent rotation therebetween.

Preferably breathing apparatus to which the filter connects is a face mask or a blower unit.

In a positive pressure or sealed mask breathing system, a hose is used to connect the air blow (PAPR blower) to the intake port of the masks for delivering the air to the mask. It is important that the hose connection at either end is not pulled as this could result in the hose becoming disconnected, allowing contaminated air to pass to the wearer. Movement of the wearer's head and torso during use can change the distance between the mask and the blower, which, if the hose is not long enough, could result in tension being applied to the connections. Equally, variations in the size of the user will vary the normal distance between the mask and the blower. Since it is usual to supply a standard-length hose for all users, that length must be chosen to accommodate these variations in distance between mask and blower and the hoses are therefore generally on the longer side. This has the problem, however, that there will generally be some excess slack in the hose which will cause it to protrude from the body, providing a snagging hazard.

According to a further aspect of the present invention there is provided breathing apparatus comprising breathing air supply means, a breathing mask, and an air delivery hose extending between the air supply means and the breathing mask, the air delivery hose is a stretch hose, that is one which is extendable from a collapsed length to an extended length, the hose including biasing means which biases to its collapsed length.

A breathing apparatus in accordance with the invention has the advantage that the stretch hose allows a naturally short hose to be used which avoids excess length which could form into loops and present a snagging risk, whilst allowing the hose to extend to accommodate changes in the distance between the mask and the air supply, such as through movements of the head or the body or physical size of the user.

The strength of the biasing means should be sufficient to ensure that the hose promptly and reliably retracts to its collapsed length when tension is not applied thereto, but should not be so high to make stretching of the hose difficult or uncomfortable to the user or apply too great a force on the connections on either end of the hose.

The form of the stretch hose itself is not important as long as the hose is sufficient robust to ensure integrity of the breathing air supplied thereby is maintained. Any conventional design for such a hose may be used, such as a hose which has a helically wound wire extending therealong which provides the biasing force which urges the hose to its collapsed length. The hose material itself may then be stretchable to allow an increase in the length of the hose or may be flexible to allow the material of the hose to fold on itself as the hose retracts to its collapsed length.

As the hose extends, it has a natural tendency to twist, which can cause causing kinks to appear, risking damage to the hose and also restricting the flow of air through the hose to the mask. Preferably, therefore, at least one of the ends of the hose is connected to its associated part by means of a rotatable coupling, that is one which allows the end of the hose to twist relative to the part to which it is connected whilst maintaining a secure, air connection.

As described above, modem breathing apparatus is generally modular in form so as to enable a range of different components such as filters to be provided for use with the core system.

Typically, the filters are removably attached to the system, such as the blower, by means of a threaded or bayonet coupling. This coupling point presents a potential point of ingress of contaminants into the air supply and a seal is therefore generally provided on the bottom face of the thread or bayonet fitting in order to isolate the air supply from possible contamination during use. However, the main body of the thread or shaft of the bayonet fitting could still potentially be exposed to contaminated air during use by a hazardous environment contamination can work its way down the thread or bayonet. Whilst this is not a problem during use when the filter is fitted as the contaminant will not be able to get past the filter into the air supply, when removing the filter, there is a risk that contaminants may have been deposited on the surface of a region of the filter coupling which engages in the blower. Such contaminants may then be dislodged from the surface of the filter coupling during removal of the filter, dropping into the blower body past the filter and compromising the air supply when the equipment is next used.

The present invention therefore further provides a filter coupling arrangement comprising a filter having one of a complimentary elongated male and female coupling part, and a housing to which the filter is attachable, the housing having the other of the complimentary elongated male and female coupling part, said elongated male coupling part being engageable in said female coupling part in order to secure the filter to the housing, the male coupling part having a base, an end remote from said base and coupling means provided between said base and said end which is engageable with complementary coupling means provided in the female coupling part, a first seal associated with the end of the male coupling part such that, when the male and female coupling parts are connected, an air tight seal is formed between the first end of the male coupling part and the female coupling part, and a second seal associated with the base of the male coupling part such that, when connected, an air tight seal is formed between the base of male coupling part and the female coupling part, whereby the coupling means is isolated from the surrounding atmosphere when the male and female coupling parts are connected.

A filter coupling arrangement in accordance with the invention has the advantage firstly that the provision of two seals gives a secondary layer of protection against leakage through the connection into the filtered air supply delivered to the user, and hence, for example, reduces the possibility of contamination due to a faulty seal. Additionally, however, the second seal, in isolating the connecting means from the surrounding atmosphere, prevent the possibility of contaminants being deposited on the surface of the connecting means which could become detached during removal of the filter and cause secondary contamination upon next use.

The connecting means may be a thread, a bayonet coupling or other well-known form of coupling for securing a filter to a piece of breathing apparatus. Preferably, the seals are mounted on annular flange surfaces formed at either end of the female coupling part, the female coupling part preferably being formed in the housing and the male coupling part on the filter. The reverse configuration, both for the position of the seals and the locations of the coupling parts is also possible and included within the teaching of the present application.

Battery powered respirators have an inherent problem of being unable to supply peak air demand in high activity situations due to the power restrictions generally associated with battery powered devices. Additionally, when higher airflow is used to meet peak demand, the nature of the filters that decontaminate the air means that they have a more limited duration of operation. In order to solve this problem, it is known in the art to provide a self-contained breathing apparatus that uses a cylinder of compressed air to supply the demand of the user. This approach has the drawback, however, that, cylinder volume generally restricts operational time to less than one hour of operation and has a weight penalty for the user because of the weight of the cylinder. The cost of the system is very high and special training is required due to the risk of using high-pressure air. Specialist equipment is also required to replenish the cylinders.

Another approach known in the art is to use an air line to supply air to the user. This has the drawback, however, that the umbilical connection which then permanently exists between the user and a fixed air supply port restricts the user with respect to access to some areas due to being attached to an "umbilical cord" to the power source for the air supply.

Conventional soft headtops generally use a non-breathing material that actually acts as a reservoir—when the user breathes in, any demand not satisfied by the blower is generally satisfied by the air in the headtop, this can be easily seen in normal use as the headtop expands and contracts during breath cycles. However, at very high volume breathing rates this volume is insufficient and contaminated air can also be pulled through from the outside by the loose fitting headtops. On full face masks, this reservoir does not exist and limits the amount of air available.

Accordingly, the present invention further provides breathing apparatus comprising a blower unit, a breathing mask and a hose connecting the blower unit to the breathing mask, the blower unit being operable to deliver air to the breathing mask along the hose, and further comprising a container located in-line between the blower unit and the breathing mask which acts as a reservoir from which air can be drawn by the user in higher demand situations.

The breathing apparatus in accordance with this further aspect of the invention has the advantage that the buffering effect provided by the reservoir isolates the blower and filters from demand increases from the user—the reservoir delivering the additional air required to meet the higher demand. Although this will cause the volume of air in the reservoir to diminish, this will be topped up during the exhalation phase of the user's breathing cycle when air will still be delivered by the blower but will not be drawn out by the user. Accordingly, the reservoir will act to meet a higher peak flow demand for a short period of time during the inhalation part of the breath cycle.

The reservoir may be a flexible container or may be collapsible. Furthermore, it may be connected directly to the outlet of the blower, directly to the intake of the mask, or in-line in the delivery hose. A one-way valve is preferably provided on the outlet end of the reservoir to prevent flow of air from the mask back into the reservoir. This will prevent back pressurization of the system which could still cause an increased load on the blower and also will prevent exhaled air, which will have a higher carbon dioxide content, from being fed back into the reservoir for re-breathing by the user.

In order that the invention may be well understood, there will now be described an embodiment thereof, given by way of example, reference being made to the accompanying drawings, in which.

Figure 1:
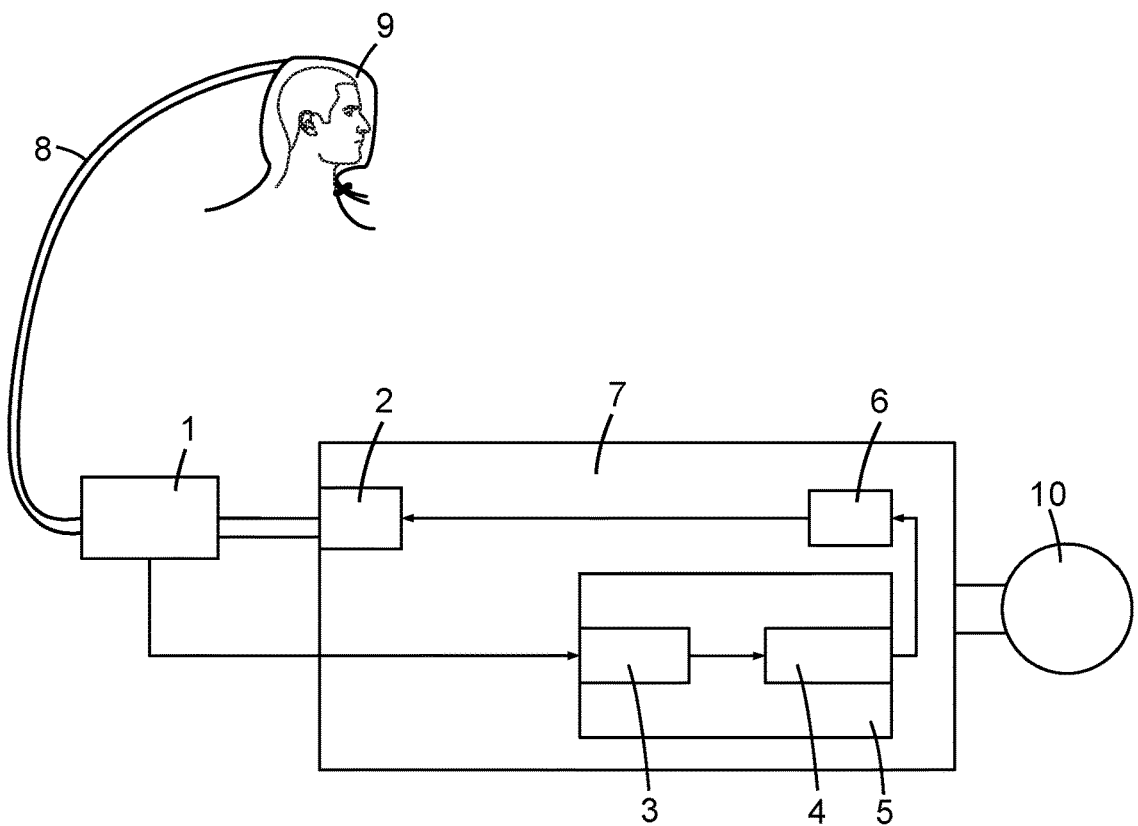
FIG. 1 is a diagrammatic representation of a typical Powered Air Purified Respirator (PAPR) incorporating a flow rate monitoring system according to the invention.

Referring first to FIG. 1, there is shown a Powered Air Purified Respirator (hereinafter PAPR) 7, of a type generally known in which filter(s) 10 are fixed to the PAPR 7 so as to filter air as it is drawn into the PAPR. The PAPR contains a motor 6 that drives an impellor in a volute 2 so as to suck air into the unit and deliver to a headtop/mask 9 via a delivery tube or hose 8.

Figure 6:
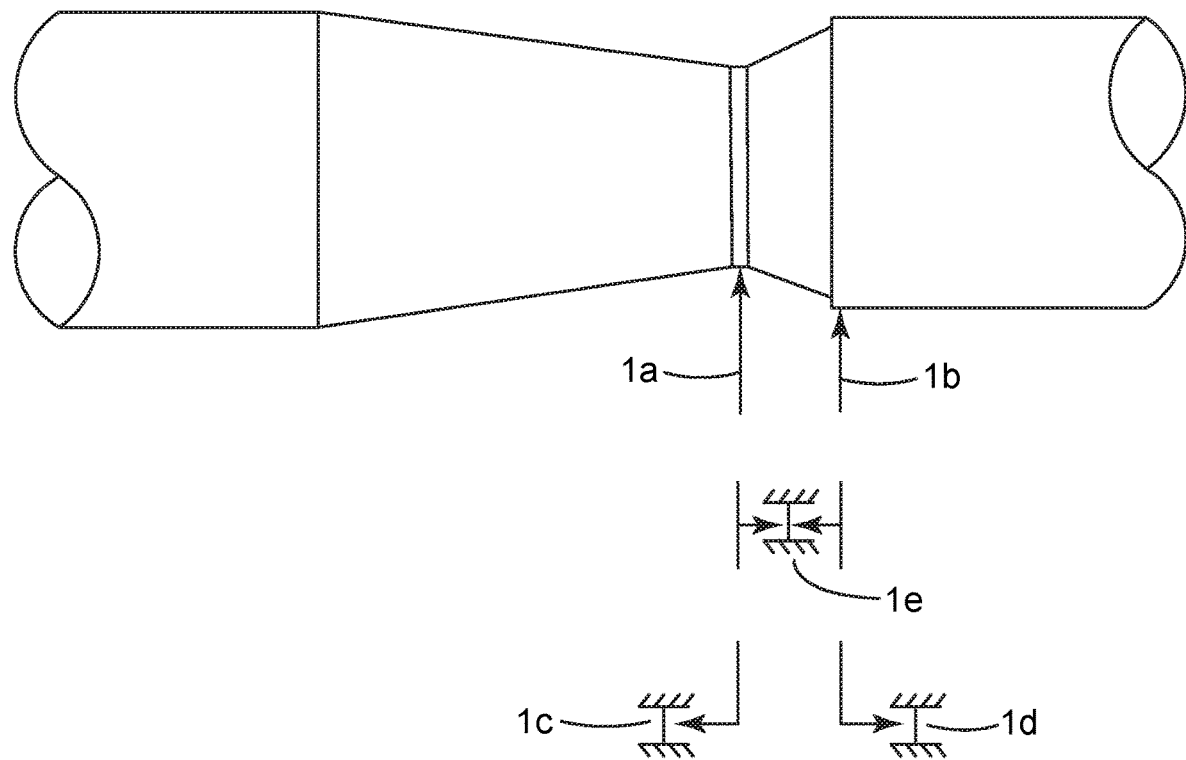
FIG. 6 is a diagrammatic representation of a dall tube which is used within the system of the present invention.

Located in line between the impeller and the headtop is a Dall tube 1 which is utilized to monitor the flow rate of air supplied to the headtop. The air supplied by the fan (impellor and volute 2) pulls contaminated air through the filter(s) 10 and pushes the breathable air through the Dall tube 1. The Dall tube 1 (shown in more detail in FIG. 6) has two pressure sensing points—a high pressure sensing point 1a and a low-pressure sensing point 1b, that connect to a pressure differential sensor which sends a signal to a signal conditioning block 3. The pressure differential sensor may be composed of two pressure sensors 1c, 1d whose readings are then used to obtain a pressure difference. Alternatively, a pressure differential sensor 1e may be used which directly measures the pressure difference between the two points by provision of a fluid connection from the pressure sensing points to opposing sides of a diaphragm in a well-known manner.

In the illustrated embodiment, the signal conditioning block 3 is mounted on a control PCB 5 inside the PAPR 7. The Dall tube may be contained within the PAPR 7 or may be an external unit thereto as illustrated in FIG. 1. Either analogue or digital based signaling may be used to feed into the signal conditioning device. The pressure pick up points in the Dall tube 1 may also optionally have an inline mechanical filtering device that reduces pressure fluctuations caused by turbulent flow in the Dall tube between the Dall tube and pressure differential sensor. Alternatively, a laminar flow device may be used within the Dall tube to reduce the turbulence. A motor drive and speed control 4 is also provided as the closed loop part of the system that controls the motor speed to reach or maintain a targeted air flow.

The air flows through the impellor and volute 2, passes through the Dall tube 1 and proceeds via an air delivery tube 8 to be delivered as breathable air to the user wearing the headtop 9. In an alternative embodiment that is not illustrated, the system could be mounted inside a face mask that also has an integral fan assembly with the filter fitted directly to the mask or connected by a tube.

The use of the Dall tube 1 enables true air flow to be measured based on volumetric flow rate that is critical as relating to filter capability. The system is also energy efficient system so as to minimize the impact to operating time on battery powered devices. Using this true air flow measurement, the true closed loop system controls actual air flow rather than calculated air flow and automatically compensates for different resistances of different filters, headtops etc. The system also compensates for breathing pattern effects on the flow rate, and altitude compensate is also built in.

It will, of course, be recognized that the pressure differential sensor may be used in other parts of the system, for example either side of the filter, in the fan assembly or in the headtop. Two completely separate pressure sensors could also be used instead of a single pressure differential sensor.

The pressure sensors of the described system could also be used to provide a breath responsive PAPR unit, as compared with prior art breath responsive PAPR systems which typically use headtop or mask pressure to identify the breathing cycle by identifying low pressure as the breathing in cycle and the high pressure as the breathing out cycle.

Figure 3A:
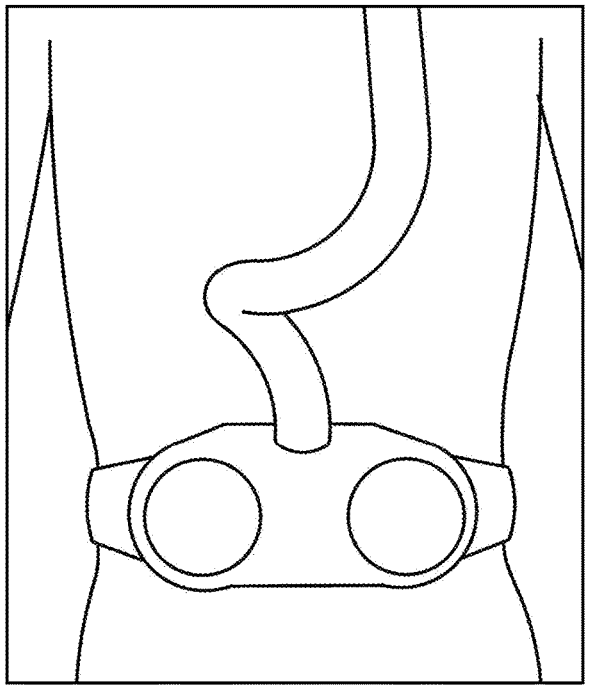
FIGS. 3a and 4a are rear and side elevations respectively of a prior art blower with a fixed hose arrangement.
Figure 4A:
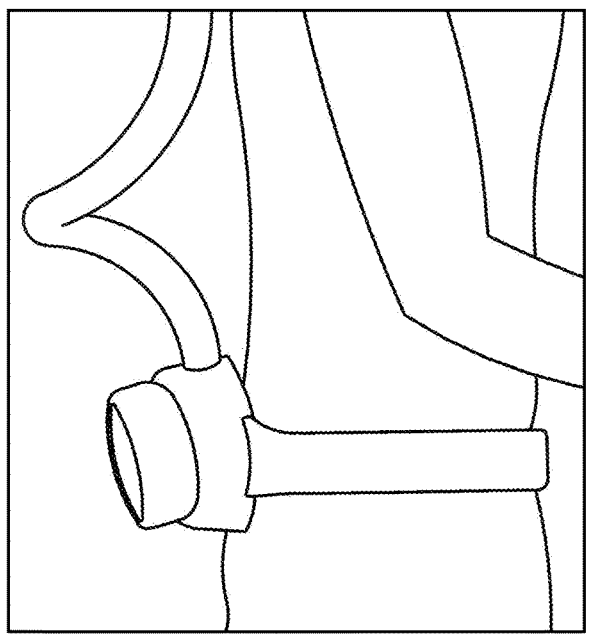
Figure 3B:
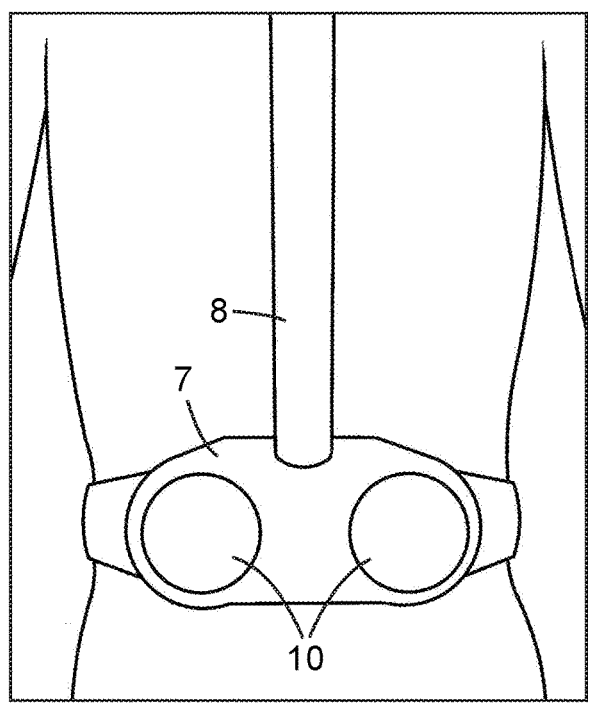
FIGS. 3b and 4b are rear and side elevations respectively a blower incorporating a stretch hose according to the present invention.
Figure 4B:
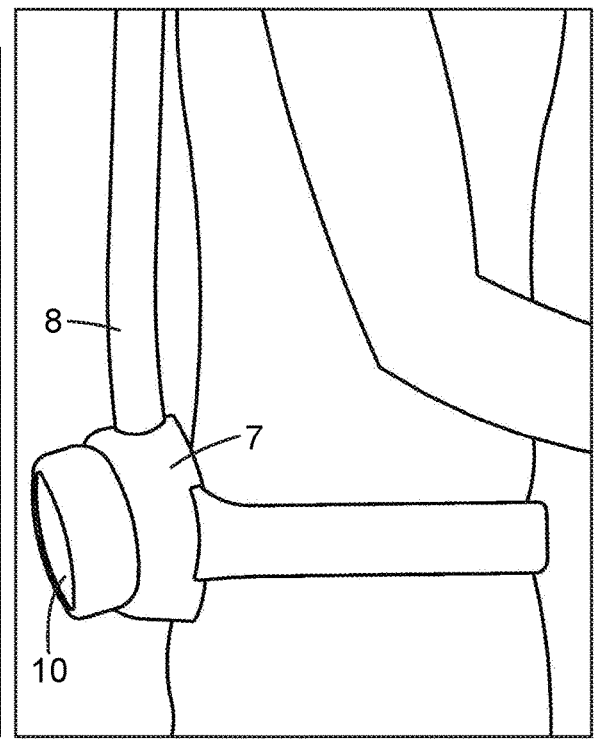

The delivery tube/hose 8 takes the form of a stretch hose, as illustrated in FIGS. 3b and 4b, that is one which is biased into a shortened retracted length and which is extendable from said retracted length against a retracting biasing load. In a well-known manner, the hose 8 is formed with a helical wire which extends the length of the hose and is wound so as to form a helical spring which has a natural retracted shape, the spring force collapsing the material of the hose onto itself to retract the hose whilst being easily extendable by simple pulling of the ends away from each other. It will, of course, be recognized that other configurations of retractable tube I hose may also be used.

The hose 8 is chosen to have a retracted length which is no longer that the shortest distance which can exist between the ports to which the two ends of the hose 8 are to be connected (in the embodiment of FIG. 1, the shortest distance between the port on the outlet of the Dall tube 1 and the port on the headtop 9). As the distance between these two ports varies during use, for example as a result of head or body movements, due to the equipment being used by a taller person or the like, the hose extends to permit comfortable use by the wearer. The hose then retracts as the distance shortens so as to ensure that there is no slack in the hose which could form loops which might be prone to snagging as illustrated in FIGS. 3a and 4a. One or both ends of the hose is/are connected to its associated port by means of a twist coupling which allows free rotation of the hose end relative to the port. The form of such a twist coupling is well known in the art and will not be described in further detail here. This accommodates the natural tendency of the hose to twist as it extends I retracts, eliminating the risk of kinking which could cause a snagging hazard.

Figure 5A:
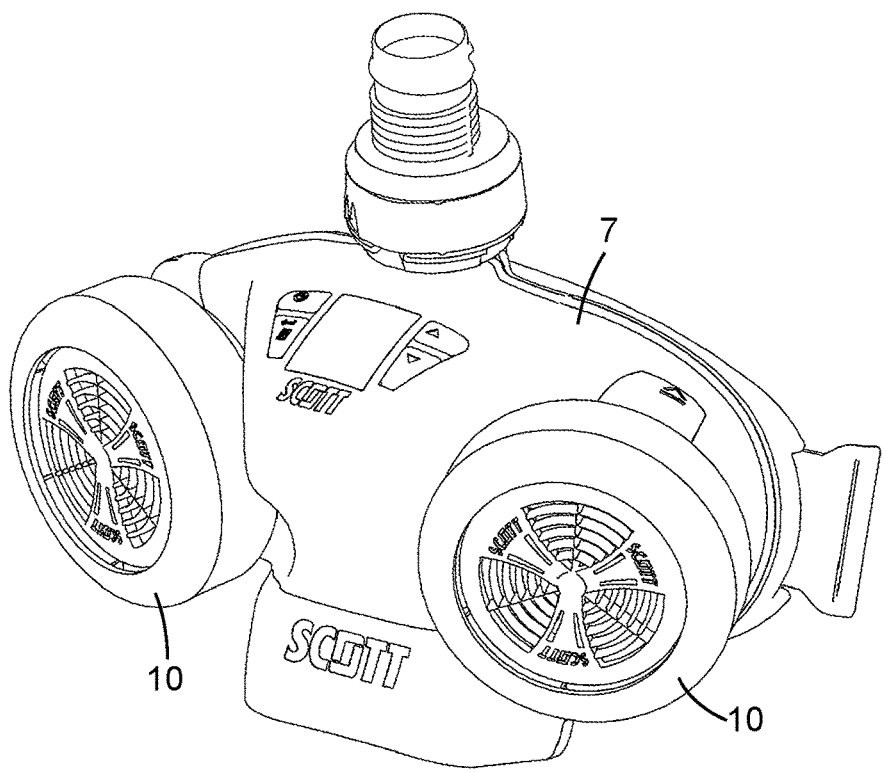
FIG. 5a is a perspective view of a blower unit which forms part of the invention.

Each filter, as shown in FIG. 5a attached to a blower unit, is removably connectable to a port of the blower unit in order to easily enable filters to be replaced, either due to operational like having expired or because different filter characteristics are required. In the illustrated embodiment, as shown in more detail in FIGS. 5b and 5c, each filter port 11 on the blower unit 7 has a female thread 12 formed on its inner cylindrical surface which complements a male thread formed on an engagement shaft of the filter 10 so as to enable the filter 10 to be screw connected to the port 11. The filter port furthermore includes a radially extending locking peg 13 which locates in a radial aperture 14 formed in the inner cylindrical surface of each filter port 11. Biasing means such as a compression spring 15 cooperates with the locking peg 13 to urge it radially inwards such that it over laps the female thread 21 and forms and obstruction therein. In particular, in the illustrated embodiment, the locking peg 13 is carried on a floating ring 13a that is urged by the action of the spring 15 into a first position in which the peg 13 is moved radially inwardly. By moving the ring 13a against the load of the biasing spring 15, the locking peg 13 is movable radially outwardly against the biasing load of the biasing means, through operation of a release lever accessible to a user on the exterior of the blower unit, so as to withdraw it from the female thread and thereby remove the obstruction.

The engagement shaft of each filter 10 has a recess 16 formed therein extending from the threaded outer surface and shape to receive the locking peg 13.

In order to fit a filter to the port, the male thread on the filter is aligned with the female thread 12 on the port 11 and the screw screwed together. When the leading edge of the male thread reaches the locking peg 13, the tapered formed of the start of the thread develops a camming action with the end of the peg 13, pressing it and hence the ring 13a outwards against the load of the biasing means into a withdrawn position in which the peg 13 no longer obstructs the female thread and the filter 10 and be further screwed into the port. It will be recognized that instead of the pin automatically being moved to a withdrawn position as the filter is screwed into the port, manual withdraw by the user by operation of the release lever may instead be necessary to enable the filter to be fully screwed into the port.

The recess 16 formed in the engagement shaft of the filter 10 is position so that it aligned both axially and circumferentially with the locking pin 13 when the filter is fully engaged in the port 11, allowing the pin 13 to snap inwards into the recess under the force of the biasing means and hence locking the filter against further rotational movement relative to the port 11, either inwards or outwards. In this way, accidental removal or loosening of the filter, which could allow contaminated air to leak through the threads and into the air supplied to the use, is prevented.

In order to remove the filter, the user operates the release lever to manually move the ring 13a against the load of the spring 15 and hence withdraw the locking peg from the recess 16 in the engagement shaft. Only with the peg 13 is moved to a fully withdrawn position will the filter be released for rotation in order to unscrew the filter from the port. This system therefore offers a significant improvement in security against accidental release as compared with prior art systems in which locking means merely required an increased initial torque to be applied to the filter in order to release the locking means and enable the filter to be unscrewed.

It will be understood that whilst the illustrated embodiment has a threaded coupling between the filter and the port, other forms of coupling may also be used within the scope of the invention, such as a bayonet type rotational coupling, it being important merely that positive intervention is required by the wearer in order to withdraw the locking peg before the filter can be released or loosened in the port.

Figure 5B:
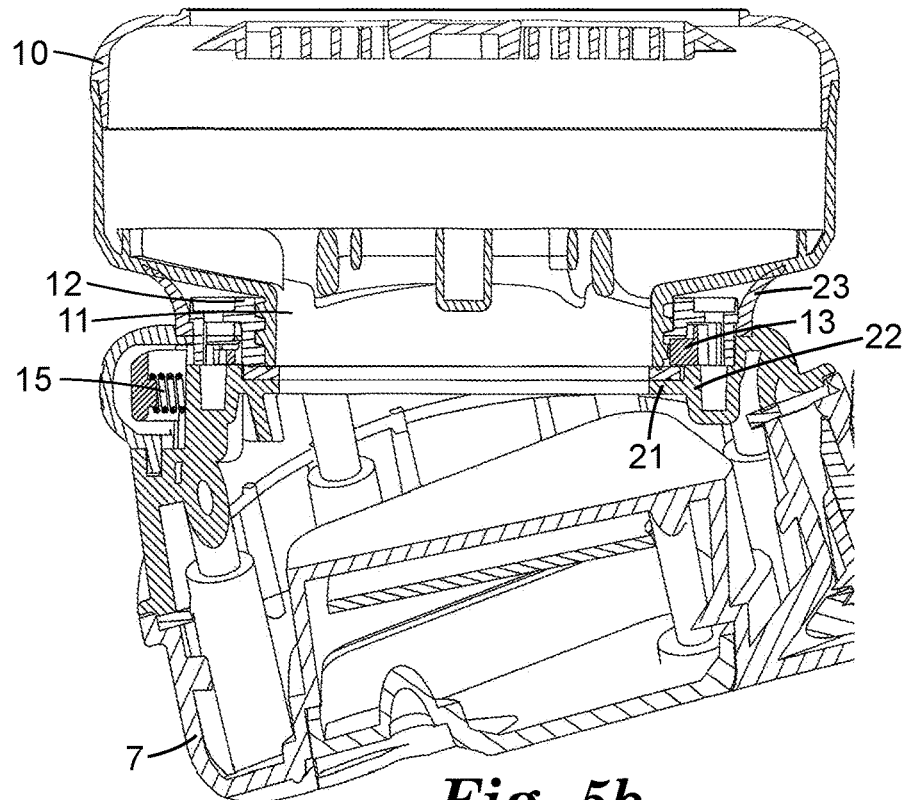
FIG. 5b is a section view through one of the filter ports of the blower showing a sealing system which forms one aspect of the invention.
Figure 5C:
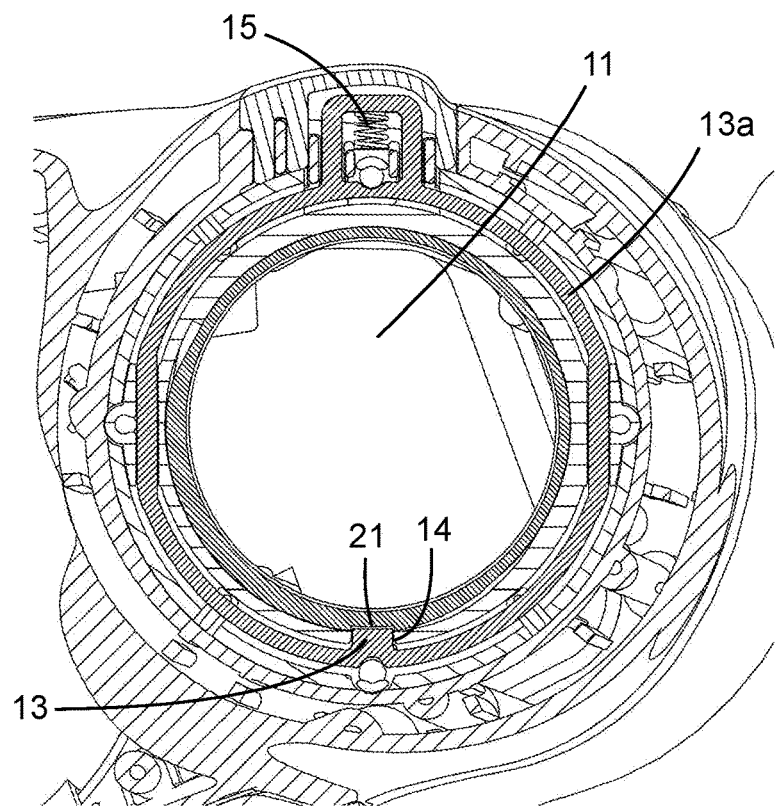
FIG. 5c is a section end view of one of the filter ports of the blower unit showing a positive lock system which forms one aspect of the invention.
Figure 5D:
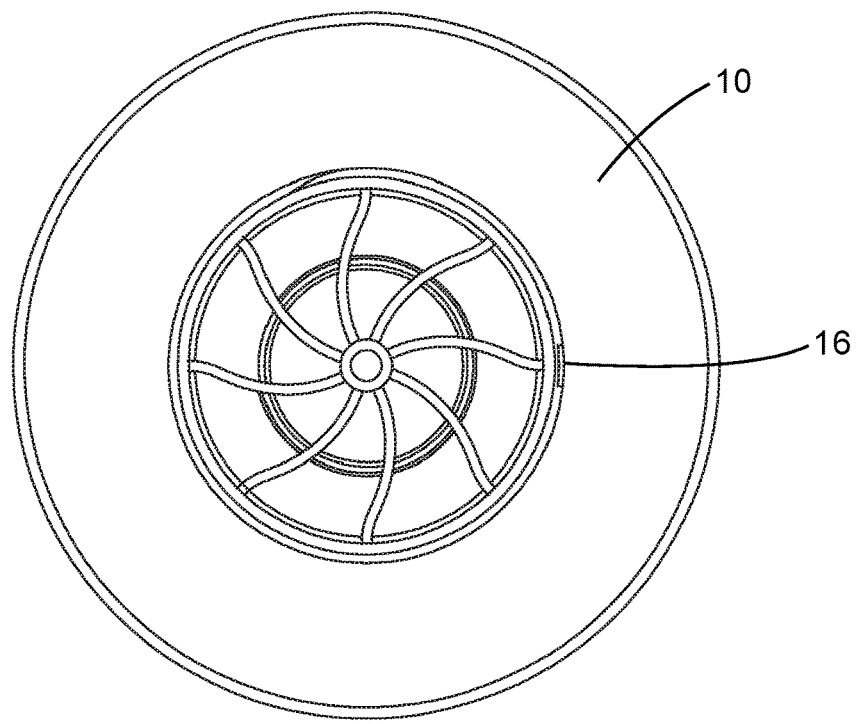
FIG. 5d is an end view of a filter incorporate a recess for interface with the positive lock system shown in FIG. 5c.

It can also be seen from FIGS. 5b and 5c that the filter port 11 is provided with a pair of seals in order to ensure there is an air tight connection between the filter and the port. More particularly, a first seal 21 is located on a face of a circumferential flange 22 formed at the bottom of the port 11 as is conventional in the art, the end of the engagement shaft of the filter 5 tightening against the first seal 21 in order to form a primary barrier against the ingress of contaminated air between the filter and the port and into the clean air passage within the blower unit. The drawback with systems which include just a single seal at this location is that both the male and female threads will still be exposed to a degree to contaminated air which can result in contaminated deposits being left thereon. As the filter is removed, these deposits can be dislodged and drop through the filter port and into the air delivery chamber inside the blower, contaminating the air delivered to the user on next use.

The present system therefore has a second seal 23 associated with each port 11 mounted on an upwardly facing surface of the port located above the thread 12 formed in the port. The second seal 23 is formed as a skirt seal which tapers outwardly away from the top of the seal port. As a filter is engaged onto the port, the skirt seal engages with the bottom face of the filter as shown in FIG. 5*b*. The secondary seal thereby isolates the thread of both the port and the filter from the contaminated air, thereby eliminating the risk of secondary contamination of the clean air delivered to the user.

The safety of the PAPR of the invention is further improved by means of a controller which is able to monitor the various components which are attached to the system and confirm suitability for use, generally as well as with each other and by any particular operator. The controller is also able to monitor and record operational time to enable user exposure information to be logged as well as equipment operating times for service purposes and the like.

This is achieved by means of the controller having a reader which is able to read a data tag associated with each component (filter, headtop etc.) connectable to the system for operational purposes. The data tags for the individual components may, for example, be RFID tags which are read wirelessly by the reader or may be some other form of ROM or flash memory which is read by wireless means or by a direct connection, for example using contacts on the components. In each case, the data tag will be programmed with information relating to the component with which it is associated, such as category (filter, headtop etc.), type (e.g. grade of filter), operating hours left before next service and the like.

Furthermore, each user will be equipped with a data tag in the form of a tally key which carries information relating to that user. Again, this is readable by the controller in a well-known manner, by direct contact or wirelessly. The tally key will be individual to the user and will store information such as equipment which he/she is trained/authorized to use, operating time on equipment, preferred setting for equipment and the like.

In use, then, the various components will be connected together ready for use and the system switched on. The controller will first of all carry out a check to make sure that all components are properly connected by carrying out an initial polling of the data tags of the components and also by some direct continuity check. The system will furthermore carry out a check to ensure that all the components are compatible with each other. For example, if incompatible filters intended for different environments are connected to the ports of the blower, it could result in contaminated air being delivered to the user as in each environment only 1 of the filters would be providing effective filtering. In the event that incompatibilities are identified by the controller, it will not allow the blower unit to start so as to prevent use, instead activating an alarm to signal a fault.

Prior to allowing use, the system will also require a user's tally key to be logged with the controller. The controller will read the user specific data from the tally key and perform an initial check to ensure that the user is properly qualified/authorized to operate the various components which are connected to the unit and also to set any operating parameters and/or restrictions which are applicable to that user (e.g. maximum time in a particular environment). Once all these checks have been completed successfully, the controller will allow operation of the equipment. Furthermore, the controller could start and then check as before and then alarm if something is wrong.

Once the equipment IS operational, the controller will then continue to gather vanous component data during operation, recording the time during which the equipment is operational, air flow rates etc., checking the data against the settings prescribed for each component and/or the particular user and activating an alarm in the event that any parameter for either the equipment or the user is exceeded (e.g. maximum air flow rate for a particular filter is exceeded). The controller also continuously monitors the status of the various components during operation of the system to ensure that they all remain properly connected throughout operation of the equipment.

The data gathered by the controller is recorded to keep a record of time of use of each component as well as period of time during which the operator has been using the equipment. The information may be recorded in a central database which is linked to the equipment/user by the unique ID carried on the memory device for each component or user. Alternatively, the data may be written back to the memory device of the associated component or user for independent storage.

In summary, the electronic storage medium of the system can be utilised to:

1) Ensure all filters are fitted and match before the product can start.

2) Check filters are not removed during use, and alarms if missing.

3) Enforce single use for filters.

4) Recognize headtops, similar features to filters.

Furthermore, the user unique second storage device/tally key can be utilized to:

1) Store user ID and product operating parameters/restrictions.

2) Log User data during use to identify the user and extent of use of the product, usage being written back to the chip, stored on the product or both (this is particularly useful for accountability reasons).

3) Store product operating parameters, so that should the user change the product (gone for repair, service etc.), he does not have to reprogram operating parameters and can just use the next product straight away.

4) Restrict Users to use only the types of equipment (filters, headtops etc.) they have been trained and certified to use.

5) Record and check Service/Inspection Status.

6) Use a real-time clock to count down and warn of when a service or safety inspection is required.

7) Ensure that unit is not used until a required service or inspection is carried out.

8) Make/keep a log of safety visual inspections using the ID of the Tally Key.

PAPR units generally have either a time duration warranty or motor life warranty. By using a real-time clock, the system of the invention can enable warranty automatically to start after a given run time, for example one hour, the start date and time then recorded as the start of the warrant and also servicing periods (rather than from manufacture date). Thus, the run time can be recorded ensuring either criterion is met. This allows for products left on the shelf at distributors etc. Additionally, a user can be warned when warranty will expire or when it was initiated.

As discussed above, the controller has various circumstances in which it may need to activate and alarm to alert the user of an issue which needs attention. In the system of the invention this alarm includes a vibration alarm which may take any of a number of forms which would be well known to the skilled person in the art. For example, an electric motor having a weight eccentrically mounted on its output shaft which causes the whole motor to vibrate as it rotates. The vibration alarm is preferably located within the PAPR blower unit, which, typically being carried on the back of the user, will be detected particularly easily by the user. However, other locations are also possible in other embodiments. In an alarm situation arising, the controller with switch on the motor which will cause the whole blower unit to vibrate. This will, then, be detected by the wearer regardless of whether he has sight of the unit. Equally, there is no possibility of mis-identifying an alarm as being from another user's unit.

A further feature of the system of the invention is the use of a display located in an area where it will be clearly visible to those surrounding and at a distance from the user. In particular, the display may be mounted in a prominent position on the blower unit or on the headtop itself or on a separate piece of equipment that could be body mounted. The controller is connected to the display either directly or wirelessly and is able to control and change the background color depending on the environment for which the whole system has been set up for use (based, for example, on the type of filter etc.). For example, if one of the filters connected to the blower is of a first grade suitable for a medium risk environment, even if the rest of the equipment is suitable for higher risk environments, the system will change the background color of the display to one corresponding to suitability for the medium risk environment only as the system is only safe to use up to that level.

The use of this display system enables a supervisor easily to check that the correct equipment is being used in any particular environment without necessarily having to be close to the user or even to enter the environment, the display giving clear visual guides if an operator is in the wrong area or using the wrong equipment.

Figure 2A:
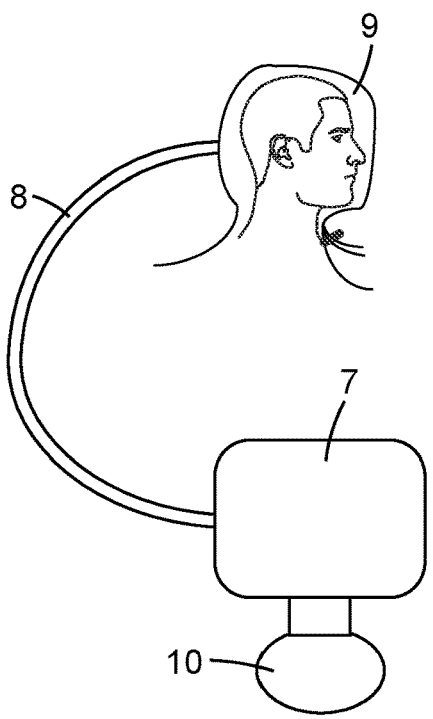
FIG. 2a is a diagrammatic representation of a prior art PAPR having a direct hose connection between blower and headtop which is shown as a hood but could also be a mask.
Figure 2B:
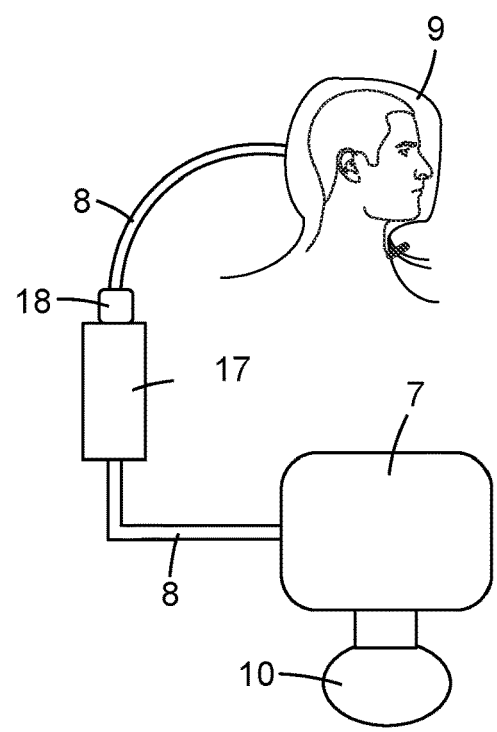
FIG. 2b is a diagrammatic representation of a system according to another aspect of the invention in which a reservoir is located in line between the blower and the headtop which is shown as a hood but could also be a mask.

As shown in FIG. 2b, in an embodiment variant, a reservoir 17 is located in line between the PAPR and the head unit. Battery powered respirators have an inherent problem of being unable to supply peak air demand in high activity situations due to the power restrictions generally associated with battery powered devices. Additionally, when higher airflow is used to meet peak demand, the nature of the filters that decontaminate the air means that they have a more limited duration of operation. The reservoir 17 is used in the invention to meet peak demand and generally to provide normal volumes of air so as to increase the life of the filters.

The reservoir 17 stores air that is replenished during either an exhalation phase of the user's breathing cycle or lower demand phase. The reservoir 17 is then used to increase the air supply at peak demand without necessitating increasing the flow of air into the PAPR through the filters, thereby reducing power demands by the PAPR and also increasing the life of filters which are not subjected to the higher flow rates.

The reservoir stores air at low pressure reservoir (the pressure achievable by the blower unit). The reservoir may be a light inflatable "bag" or a flexible light weight container, the volume of which is chosen to meeting high demand rates in line with the amount of air that the blower can provide—so for low flow rates from the blower this reservoir need to be larger, but for higher flow rates it would be smaller.

A one-way valve 18 is located on the headtop end of the reservoir 17 which ensures that exhaled air which has a higher carbon dioxide content does not enter the reservoir, thereby preventing the user from re-breathing exhaled air.

The invention claimed is:

1. A breathing apparatus comprising:
 a blower unit;
 multiple components removably coupled to the blower unit, the components including at least a filter mounted to the blower unit and a face mask coupled to the blower unit via a hose, at least one of the components having a component data tag affixed thereto, the component data tag storing component information associated with the at least one of the components to which the component data tag is affixed, the component information including at least one of a category of the at least one of the components or a type of the at least one of the components; and
 a controller communicatively coupled to the blower unit, the controller communicatively coupled to a reader that is configured to read the component information stored on the component data tag, the controller further configured to process user information that is associated with a user of the breathing apparatus, wherein the controller is configured to process data of the component data tags and the user information and to determine, based at least on the category or the type the component, whether the user of the breathing apparatus is associated with the blower unit, and, responsive to determining that the user is not associated with the blower unit, the controller is configured to perform at least one operation.

2. The breathing apparatus of claim 1, wherein, responsive to determining that the user is not authorized to operate at least some of the components that are coupled to the blower unit, the controller is further configured to generate an output.

3. The breathing apparatus of claim 2, wherein the output is a vibration alarm disposed in the blower unit, the vibration alarm configured to vibrate upon activation to cause the blower unit to vibrate and be detected by a user that is carrying the blower unit.

4. The breathing apparatus of claim 1, wherein, responsive to determining that the user is associated with the blower unit, the controller is configured to allow the blower unit to be operable such that the blower unit is able to be started by a user.

5. The breathing apparatus of claim 1, wherein to perform the at least one operation is to generate an output.

6. The breathing apparatus of claim 5, wherein the output is at least one of a notification or logged data.

7. The breathing apparatus of claim 1, wherein to perform the at least one operation is to not allow the blower unit to be operable.

8. The breathing apparatus of claim 1, wherein the user information includes user authorized equipment, and wherein to determine whether the user of the breathing apparatus is associated with the blower unit is to determine, using the user information, whether the user of the breathing apparatus is authorized to operate the blower unit.

* * * * *